United States Patent [19]

Lund

[11] 4,313,443

[45] Feb. 2, 1982

[54] POCKET ECG ELECTRODE

[76] Inventor: Robert A. Frosch, Administrator of the National Aeronautics and Space Administration, with respect to an invention of Gordon F. Lund, San Jose, Calif.

[21] Appl. No.: 185,865

[22] Filed: Sep. 11, 1980

[51] Int. Cl.³ .............................................. A61B 5/04
[52] U.S. Cl. .................................................. 128/642
[58] Field of Search ................ 128/639, 642, 784, 785

[56] References Cited

U.S. PATENT DOCUMENTS

| | | | |
|---|---|---|---|
| 3,476,116 | 11/1969 | Parsonnet et al. | 128/784 |
| 4,031,882 | 6/1977 | DeLuca | 128/642 |
| 4,219,027 | 8/1980 | Lund | 128/642 |

*Primary Examiner*—William E. Kamm
*Attorney, Agent, or Firm*—Darrell G. Brekke; John R. Manning

[57] ABSTRACT

A low-noise electrode suited for sensing electrocardiograms when chronically and subcutaneously implanted in a free-ranging subject. The electrode comprises a pocket-shaped electrically conductive member with a single entrance adapted to receive body fluids. The exterior of the member and the entrance region is coated with electrical insulation so that the only electrolyte/electrode interface is within the member remote from artifact-generating tissue. Cloth straps are bonded to the member to permit the electrode to be sutured to tissue and to provide electrical lead flexure relief.

7 Claims, 6 Drawing Figures

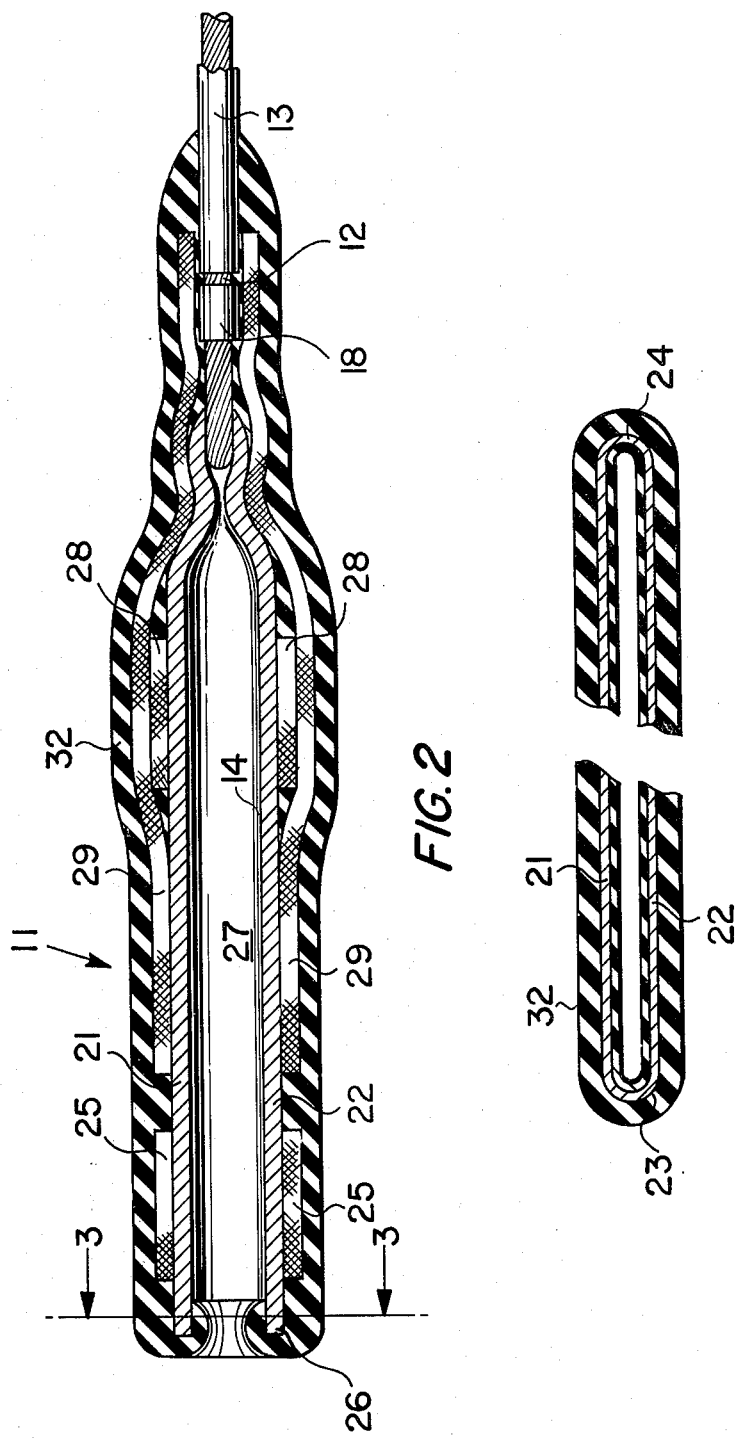

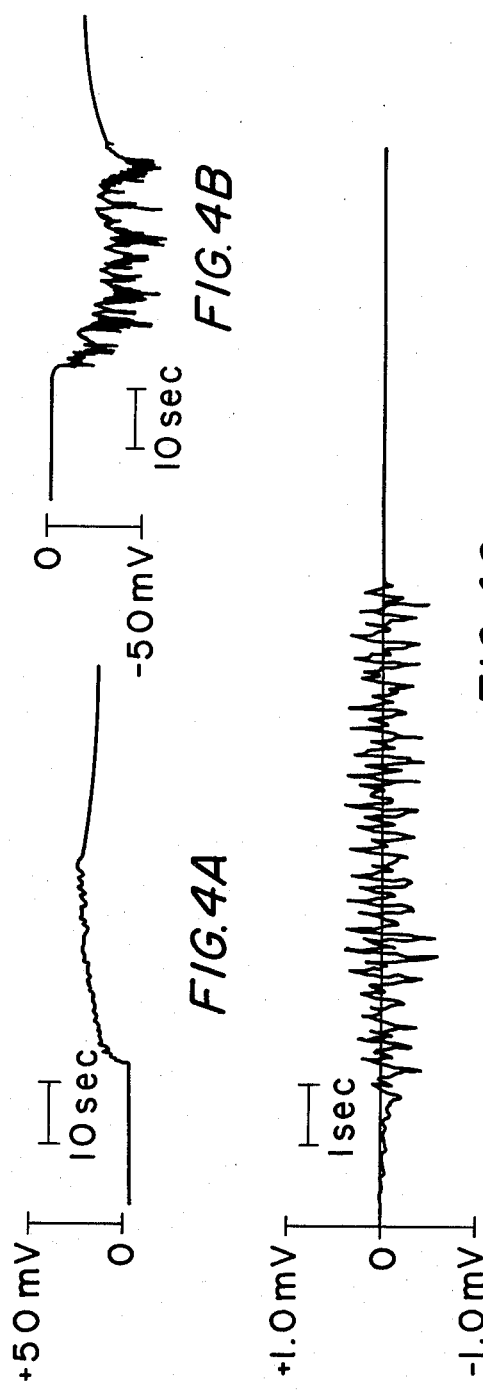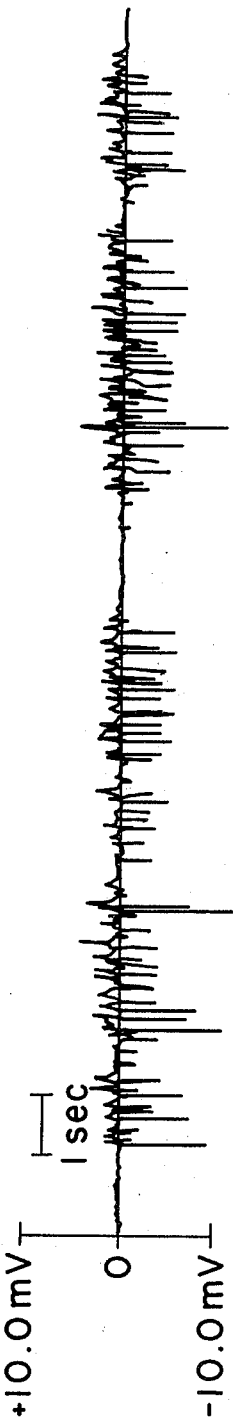

POCKET ECG ELECTRODE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

TECHNICAL FIELD

The instant invention relates in general to subcutaneous electrode structures and, more particularly, to an improved recording-type electrode structure particularly useful as a chronic implant for sensing electrocardiograms of active subjects.

BACKGROUND ART

Heart rates and body temperatures are substantially influenced, either directly or indirectly, by both the autonomic and central nervous systems, by the endocrine system, and by metabolism. Heart rate and temperatures, particularly in combinations, can therefore inherently serve to index many and various interactive responses of animals to their environments. These responses include changes in activity, emotions, health, energy allocations, behavioral patterns, and biological rythms. To develop indices based on physiological parameters, such as heart rate and body temperature, to assess animal responses it is often necessary to continuously record the parameters for long periods. The changes that are then observed can be related to the context of the experiment and to the stimuli that gave rise to the responses.

Radiotelemetry has made it possible to monitor physiological parameters in unrestrained subjects for long test periods. Considerable effort has been made to develop biotelemetry systems small enough to be implanted in the most commonly used laboratory animals. U.S. Pat. No. 3,453,546, July 1, 1969, Thomas B. Fryer for example, reveals an implantable telemeter capable of measuring temperature and pressure.

Difficulties have been encountered in finding suitable electrodes for providing ECG biopotentials in active unrestrained subjects wherein the electrodes are chronically implanted. When conventional ECG electrodes are moved, artifacts are generated which tend to mask the desired biopotentials. If the biopotentials are very weak, it may be impossible to distinguish them from the artifacts. It has been found that when intracardial stimulating electrodes are used for detecting biopotentials, artifact generation is usually more pronounced than it is with standard implantable ECG electrodes.

There is more information available on external ECG electrodes than internal ones. In the past, designers of external electrodes worried about maintaining a high load-to-source impedance ratio to prevent amplifier loading, signal distortion and extraneous 60-Hertz noise. Therefore, they chose external electrodes with large distributed surface areas in order to compensate for the high contact impedance caused by the cornified epithelium of the skin. Of course, as the electrode area was increased, the contact impedance was reduced. Electrolytic pastes and jellies were also employed to reduce the contact impedance. Internal electrodes do not encounter a cornified epithelium and they are rarely bothered by 60-Hertz stray noise. The body fluid that engulfs the electrode when it is implanted in tissue serves an an electrolyte. Investigators such as Geddes and Baker have stated that subcutaneously implanted stainless steel needle electrodes have a low enough impedance to prevent amplifier loading and signal distortion (Med. & Biol. Engng. Vol. 4, pp. 439-450, Pergamon Press, 1966).

The typical approach to the internal electrode artifact problem has been to provide an electrode of a very small surface area which could be securely anchored against the tissue. Electrodes of this type have included small hooked wires, needles and wire loops. Electrodes and the Measurement of Bioelectric Events, L. A. Geddes, John Wiley and Sons, New York 1972; Introduction to Bioelectrodes, C. D. Ferris, Plennum Press, New York 1974; and Medical Instrumentation, Application and Design, J. G. Webster, ed., Houghton Mifflin Co., Boston 1978. A departure from this philosophy is found in U.S. Pat. No. 4,219,027 which discloses a smooth, stainless steel disc ECG electrode.

Body-implantable electrodes for the intracardial stimulation of a heart are revealed in the following U.S. Pat. Nos. 3,664,347; 3,788,329; 3,804,098; 3,911,928 and 4,135,518. These patents all show endocardial electrodes housed in flexible catheters. Intracardial electrodes are used with pacemakers and they are often designed with very small electrode areas to minimize the current flux and the drain on the pacemaker power supply.

DISCLOSURE OF INVENTION

The principal object of the present invention is to provide an improved subcutaneous ECG electrode useful for chronic implant in active subjects.

Another object of the instant invention is to provide an improved electrode with a large smooth surface area for an electrode-electrolyte interface; and one in which the interface is isolated from an artifact-generating environment in a manner that does not force the desired ECG currents to reach the interface via a constricted current path. It is yet another object of the present invention to provide an ECG electrode featuring tissue-compatible materials and whose shape minimizes trauma to the subject. It is still another object of the invention to provide an ECG electrode with means for reducing flexure stress on the conductive lead fastened to the electrode and obviating tissue pressure points in the region where the lead connects to the electrode.

In order to overcome the deficiencies of the prior art devices, and in order to achieve the foregoing objects, the present invention comprises a pocket-shaped electrically conductive member with a large mouth adapted to permit the influx of body fluid so that electrical currents produced by the ECG biopotentials may reach the inner surface of the member. The member has the appearance of a squashed cylinder that is open at one end and closed at the other end. An electric lead capable of conveying the sensed biopotentials to suitable monitoring apparatus is secured and electrically connected to the closed end of the electrically conductive member. The exterior surface and the mouth region of the member are covered with an electrical insulative coating so that the only portion of the electrode in electrical contact with the body fluid electrolyte is situated in the lumen of the pocket-shaped electrically conductive member. Thus, the electrode/electrolyte interface is removed from tissue which could rub there against and generate artifacts. The interior of the pocket-shaped member provides a large smooth area for the electrolyte/electrode interface and the mouth has a large cross-sectional area so that the interface does not see just the current flux from a small localized area where an artifact may be present.

In one feature of the invention, cloth strips are bonded to the electrode and electrical conductor with an elastomeric material for reducing stress on the electrical conductor. In another feature of the invention, cloth strips are bonded to the electrode to permit the electrode to be securely sutured to adjacent tissue.

Other features and advantages of the present invention will become apparent upon the perusal of the following specification taken in connection with the accompanying drawings.

BRIEF DESCRIPTION OF THE DRAWINGS

FIG. 2 illustrates in elevational longitudinal section the ECG electrode.

FIG. 3 is a fragmentary elevational sectional view of the mouth of the ECG electrode.

FIGS. 4A and 4C depict artifacts generated by a metal disc ECG electrode.

FIGS. 4B and 4D show artifacts derived from a wire loop ECG electrode.

DETAILED DESCRIPTION OF THE INVENTION

Figure 1:
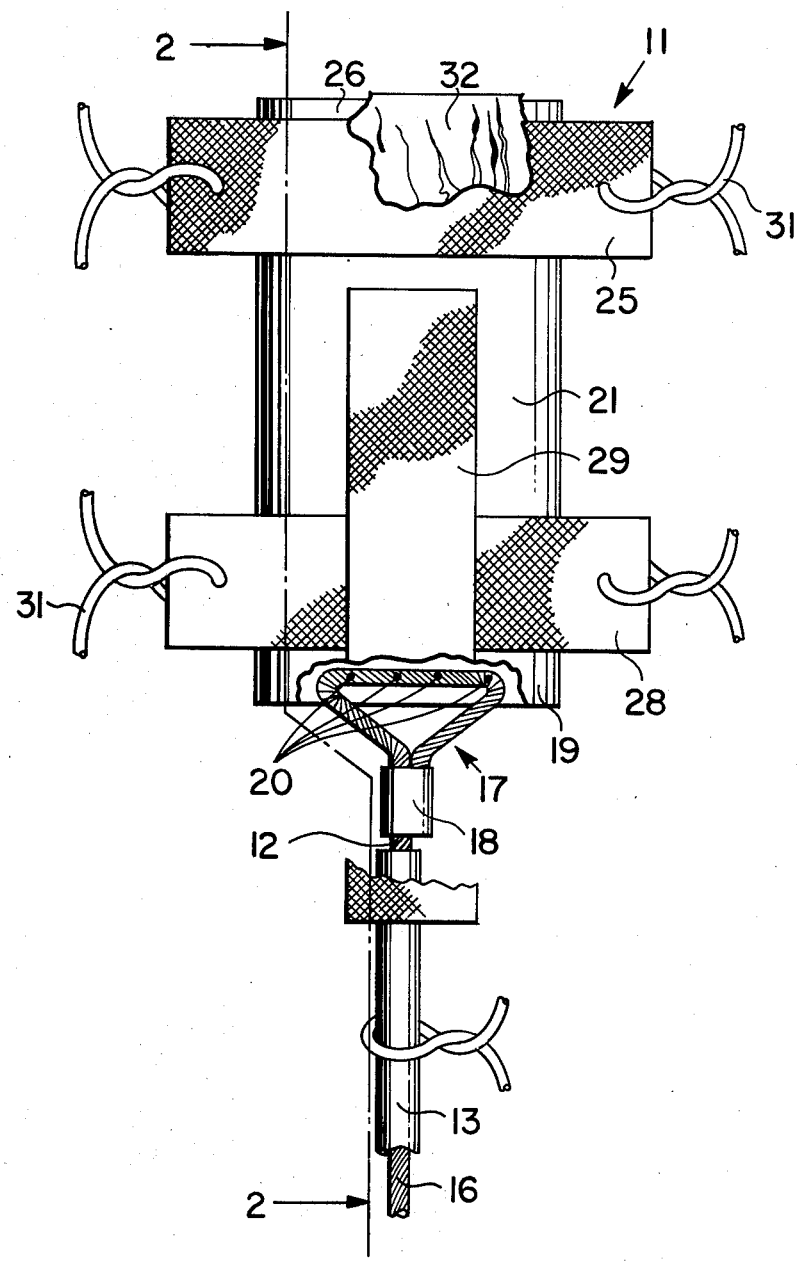
FIG. 1 is a plan view of a subcutaneous ECG electrode according to the present invention.

Referring now to FIG. 1, there is shown a subcutaneous ECG electrode 11 made in accordance with the present invention for chronically deriving electrocardiograms from an active subject. A flexible electrical conductor 12, some portion of which is covered with insulation 13 to make an electrical lead, is secured to and in electrical contact with pocket-shaped electrically conductive member 14. The conductor 12 is preferably comprised of multiple strands of stainless steel wire. End 16 of the electrical conductor is adapted to be connected to monitoring equipment such as a high-impedance input amplifier and a recorder (not illustrated). At the opposite extremity from end 16 the bare conductor is doubled back on itself to form a loop 17 and the side-by-side segments of the conductor are squeezed together and tightly encircled by a metal crimp band 18. Electrode 14 has an oval cross-section and is made up of substantially parallel and coextensive walls 21, 22 and curvilinear end sections 23, 24 (see FIG. 3). Pocket-shaped member 14 may be constructed from a flattened tube with a substantially uniform wall thickness. The common practice of using solder and solder flux to make connections to electric leads has been found to cause problems in implants. Tissue toxicity responses and deterioration of the connection due to battery potentials that arise from the metal discontinuities and flux chemistry are likely to result when soldered joints are implanted. Spot welding and crimping have been found to be better ways of making connections. After member 14 reaches the stage of fabrication where it looks like a squashed metal cylinder, electrical conductor loop 17 is inserted into end 19 of member 14, end 19 is crimped closed and loop 17 is spot welded to member 14. For example, the loop may be spot welded to member 14 at points 20. End 26 of member 14 is left open and forms a mouth or entrance to the pocket so that when the electrode is implanted body fluid may flow into the lumen or chamber 27 (see FIG. 2) and wet the interior surfaces. Thus, the body fluid which is an electrolyte, permits electric currents generated by the subject's heart to reach the inner metal walls of pocket-shaped member 14.

A material which is tolerated reasonably well by tissue and which is suitable for member 14 is stainless steel. Silver is less durable and somewhat toxic; however, it may be used as an alternative. Cloth straps 25 are glued to the outer surfaces of electrode walls 21 and 22 near electrode mouth 26. A second set of cloth straps 28 are glued to the outer surfaces of walls 21 and 22 in the proximity of conductor loop 17. A polyester cloth such as coarse woven Dacron ® has been found to be compatible with tissue. Cloth straps 29 are also placed over and normal to straps 28. These straps are adhered to member 14, straps 28 and conductor 12. Straps 29 provide stress relief for conductor 12 when forces are exerted on it in the direction away from member 14. Straps 29 also reduce the likelihood of the electrical conductor therebetween kinking and producing a tissue pressure point. Once the pocket electrode is in place in a subject, it may be secured to the subject's tissue by sutures 31. The exterior surface of member 14 as well as the mouth region, plus the cloth straps and a portion of the electrical conductor adjacent the electrode are covered with a tissue-compatible elastomeric electrical insulation 32 of very high impedance. The preferred insulation is silicone rubber and this material may also be used to glue the cloth straps to electrode 14. Further, silicon rubber may be used as insulation 13 for electrical conductor 12.

When the pocket electrode is implanted in a subject, body fluids touch the exterior surfaces and fill lumen 27; however, the body fluids are only permitted electrical contact with the interior walls of member 14. Some of the advantages of the pocket electrode are believed to derive from the creation of an electrode/electrolyte interface that is removed from tissue/electrode disturbances. The portions of the electrode that can be touched by tissue are electrically insulated. Lumen 27 can be reached by electrolytes in the form of body fluids, but only by tissue. The mouth of the pocket electrode is relatively large and the exposed electrode surface on the interior of the pocket electrode is smooth and much larger than that of a typical ECG electrode such as a lead loop electrode. Accordingly, it is believed that the path of current flux into the lumen is not unduly constricted and thus not easily perturbed, and that any extraneous localized region of cellular or mechanical activity fails to rise to a noticeable level as would be the case with a small conventional ECG electrode.

The electrode is easy to clean and to keep clean during surgery. It is not prone to tissue imbedding and thus the electrical performance tends to remain constant with time. The electrode has a thin silhouette with no objectionable protrusions. The electrical lead tends to remain flat where it connects to the electrode. Accordingly, the electrode may be subcutaneously accommodated with relative comfort and no fear of unpleasant pressure points or rejection. When implanted, the electrodes should be placed to the side of the skin incision to facilitate revascularization of the skin. The axis of incision when in the anterior-posterior plane minimally disrupts the vascular bed. Generally, the larger the size of the electrode, the more the vascularization of the overlying skin is undesirably reduced. In one experiment involving a labrador dog as a test subject, an electrode made in accordance with the subject invention was utilized and it had a wall 21 that was 2.5 cm long, 1 cm wide, and 0.010 inches thick. The experiment had a duration of three months and when the electrode was examined after the experiment it was noted that no tissue had entered lumen 27.

In vitro tests with two prior art ECG electrodes as well as the present invention were conducted to simulate the in vivo environment. Tests were performed on lead loop electrodes, disc electrodes of the type described in U.S. Pat. No. 4,219,027, and electrodes made in accordance with the subject invention. A pair of each type of ECG electrodes was immersed in an 0.9% saline bath and one electrode was rubbed between two fingers to simulate the electrode/tissue motion encountered in an active subject. The electrodes were coupled to monitoring apparatus with a 10-megohm input impedance. In one test, the monitoring apparatus included a 10–100 Hz bandpass filter whereas in another test the filter was removed and the apparatus had d-c response. FIGS. 4A and 4C depict the artifacts generated when the disc electrode was rubbed, and FIGS. 4B and 4D illustrate the artifacts that were produced when the lead loop was rubbed. The bandpass filter was employed when the artifacts of FIGS. 4C and 4D were generated. It is quite evident from the potential plots that the lead loop electrode generates more artifacts, by at least an order of magnitude, than the disc electrode. On the other hand, when a pocket electrode made in accordance with the present invention was rubbed between fingers in the saline solution, neither baseline shifts (d-c voltages) nor oscillations (a-c voltages) were observed. That is, no artifacts were generated when the electrode perturbed.

Those skilled in the art will appreciate that the specific structures and methods of operation described herein may be altered without departing from the spirit and scope of the invention.

We claim:

1. In a subcutaneous electrode apparatus for measuring electrocardiograms:
   an electrically conductive pocket-shaped member having an opening and a lumen, said member being adapted to be chronically subcutaneously implanted in the tissue and body fluid of a subject in which electrocardiograms are to be sensed;
   said opening being an elongated mouth adapted to permit body fluids to enter said lumen and contact the inner surface of said member;
   electrical conductor means including an electrically conductive wire structure for making electrical connection to said pocket-shaped member;
   means bonded to said pocket-shaped member for receiving sutures when said electrode apparatus is implanted in tissue; and
   electrically insulative means for coating the outer surface and mouth region of said pocket-shaped member whereby when the electrode apparatus is implanted the body fluid acts as an electrolyte and the electrode/electrolyte interface is situated within the lumen remote from possible tissue disturbances.

2. An apparatus as set forth in claim 1 wherein said electrically conductive pocket-shaped member has two substantially rectangular parallel coextensive metal walls.

3. An apparatus as claimed in claim 2 wherein a portion of said conductive wire structure forms a loop and said loop is secured to and sandwiched between said walls at an extremity of said pocket-shaped member remote from said mouth.

4. An apparatus as claimed in claim 3 wherein said pocket-shaped member is comprised of substantially uniform thickness metal and has the appearance of a flattened tube with one tube end closed.

5. An apparatus as described in claim 4 wherein said receiving means are straps of cloth bonded to said substantially parallel walls of said pocket-shaped member.

6. An apparatus as set forth in claim 5 wherein straps are bonded to said pocket-shaped member and said electrical conductor means to provide stress relief for said electrical conductor means when a force is exerted thereon in a direction away from said pocket-shaped member.

7. Apparatus as set forth in claim 6 wherein said pocket-shaped electrode is made of stainless steel and said electrically insulative means is made of silicone rubber.

* * * * *